Feb. 4, 1941. J. VERSCHUREN Plant Pat. 445
ROSE PLANT
Filed April 30, 1940
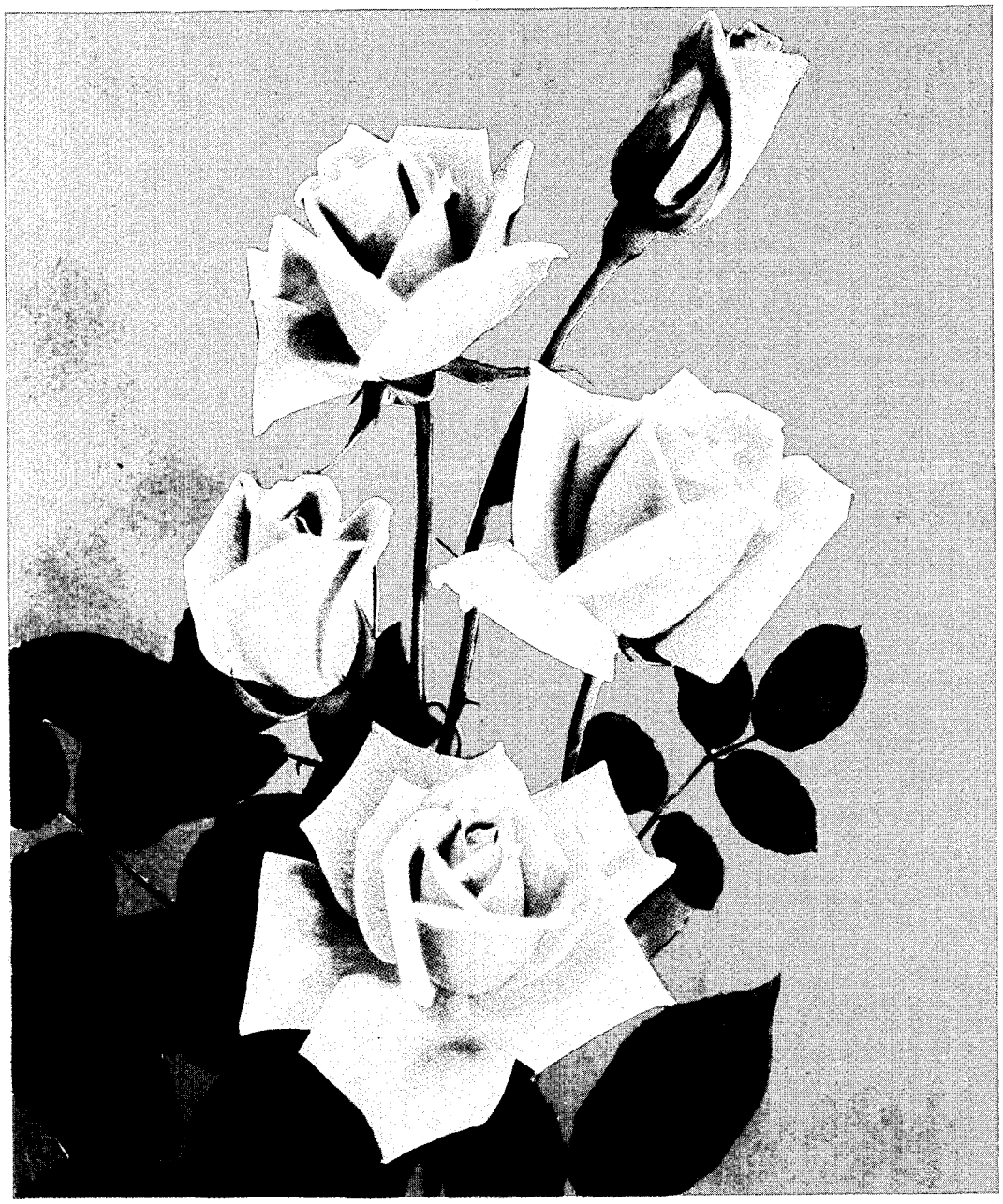
INVENTOR
Jac Verschuren
By Orville M Kile
Plant Pat. Agt.

Patented Feb. 4, 1941

Plant Pat. 445

UNITED STATES PATENT OFFICE

445

ROSE PLANT

Jac Verschuren, near Uden, Netherlands, assignor to John Parmentier, Bayport, N. Y.

Application April 30, 1940, Serial No. 332,597

1 Claim. (Cl. 47—61)

My present invention is an improvement in hybrid tea roses and resulted as a cross between the variety Briarcliff as the seed parent and an unnamed seedling as the pollen parent. The cross pollination was done by me in my greenhouses in Haps, Holland.

The purpose of the hybridization was to produce a rose highly resistant to black spot and mildew, which would at the same time be a strong grower and abundant producer. I believe I have succeeded in producing a rose with these qualities which also has a very attractive blossom of good size and form and distinctive coloring. A friend reports a test showing that this new variety was grown for one year bordered on three sides by two rose varieties which take black spot very easily and which were at times badly diseased, but this new variety never showed any signs of black spot. Neither was any mildew ever apparent on plants of the new variety.

My new variety has been reproduced asexually and its characteristics have proved to be permanent.

The original illustrations accompanying this application show five specimen blossoms of this variety in varying stages of maturity, together with a portion of the stems and leaves. These are shown in as nearly their true colors as it is possible to depict them, but it must be understood that artificial coloring does not bring out the true tones of the natural blossoms, also that there is some variation in the color according to growth conditions.

Color references are to Ridgway's Color Standards and Nomenclature, except where the usual dictionary definition is obviously intended.

Following is a detailed description of the plant and flower of this new variety.

*The plant*

Growth: Very vigorous upright bush; abundant producer; continuous bloomer; flowers borne singly.

Stems: Slender but strong.

*Color.*—Calla Green (Plate V), sometimes with a brownish tinge on the side next the sun.

*Thorns.*—Sharp; slender; moderate in number; Hydrangea Red (Plate XXVII).

Foliage: Abundant.

*Leaves.*—Compound; usually 3 to 5 leaflets, sometimes 7; veining prominent.

*Leaflets.*—Lateral leaflets almost sessile to rachis. *Size*—variable. Terminal leaflet of leaves on lower portion of stem averages 2½ to 3 inches long by about 1½ to 1¾ inches wide; leaflets of compound leaf nearest peduncle are small and more nearly round, the terminal one measuring 1½ inches by 1¼ inches. *Shape*—larger leaflets are elliptical with rounded base and acuminate apex, relatively narrow. Smaller leaflets of the leaves nearest peduncle are more nearly round. *Margin*—regularly, sharply and finely serrated; tinged with Hydrangea Red. *Color*—upper surface Elm Green (Plate XVII); under surface grayish green between Light Elm Green and Light Bice Green (Plate XVII).

*Rachis.*—Slender; on upper side grooved and tinged with Hydrangea Red; on lower side Oil Green (Plate V) and smooth with the exception of an occasional very sharp thorn.

*Stipules.*—Narrow; clinging; sharp-pointed.

Disease resistance: Particularly resistant to black spot and mildew.

*The flower*

Bud:

*Size.*—Medium, averaging 1½ to 2 inches long.

*Color.*—When tight bud it is between Peach Red and Rose Doree (Plate I); later, between Rose Doree and Geranium Pink (Plate I).

*Form.*—At first it is long-pointed; later, slender without bulge.

*Opening.*—Slow and even.

*Peduncle.*—Usually rather short; slender but strong; between Lettuce Green and Oil Green (Plate V).

*Calyx.*—Large; same color as peduncle.

*Sepals.*—Permanent; short to medium length, with long slender tips; sometimes simple but frequently with one to four side branches.

Blossom:

*Size.*—Medium, average spread 4 to 4½ inches.

*Petalage.*—From 25 to 35 petals in the month of January.

*Color.*—The combination of colors of this rose is very novel and distinctive, and the color tones are difficult to describe in standard terms. The outer surface of the petal of the blossom is much like that of the bud (described above), although slightly lighter in tone. An aiglet of Amber Yellow (Plate XVI) suffuses into this color on the lower portion of the petal. The inner surface of the petal is much lighter than the outer surface and its color lies between Grenadine Pink (Plate II) and Strawberry Pink (Plate I). The aiglet on the inner surface is approximately Lemon Chrome (Plate IV).

*Form.*—Very high-centered, opening into cup-shape and revealing stamens only in last stages of maturity. Edges of petals roll backward slightly, frequently producing triangular appearance of petal and revealing the contrast of colors between the inner and outer surfaces of the petals.

*Petals.*—*Shape*—outer petals oval, inner petals narrower progressively toward center of flower. *Size*—outer petals 1¾ inches wide by 2 inches long. *Arrangement*—tightly imbricated. *Behavior*—clinging. *Fragrance*—mild. *Longevity*—average.

*Reproductive organs*

*Pistils:* Many; bunched.

*Styles.*—Medium length; thin; upper portion approximately Jasper Red (Plate XIII); lower portion light yellow, approximately Picric Yellow (Plate IV).

*Stigmas.*—Buff Yellow (Plate IV).

*Stamens:* Many; surround pistils.

*Filaments.*—Uneven lengths; Flame Scarlet (Plate II) at base, merging into Deep Chrome (Plate III) at the tip.

*Anthers.*—Large; Deep Chrome (Plate III).

*Ovaries:* Mostly inclosed in calyx.

Having thus disclosed my invention, I claim:

A new and useful variety of hybrid tea rose plant characterized particularly by its great resistance to black spot and mildew; its strong growth; its abundant production; the very high degree of retention of form of its high-centered blossoms; and the distinctive bi-color effect of its blossoms with petals darker on the outside surface than on the inner surface, in color tones from Grenadine Pink to Peach Red, substantially as shown and described.

JAC VERSCHUREN.